United States Patent [19]

Burger et al.

[11] Patent Number: 5,102,807
[45] Date of Patent: Apr. 7, 1992

[54] INHIBIN ISOLATED FROM OVARIAN FOLLICULAR FLUID

[75] Inventors: Henry G. Burger, East Melbourne; David M. de Kretser, Surrey Hills; John K. Findlay, Mont Albert; Francis J. Morgan, North Fitzroy; Milton T. W. Hearn, Balwyn; David M. Milne-Robertson, Glen Waverley; Robert G. Forage, New South Wales, Richard Edward Hugh Wettenhall all of Australia

[73] Assignees: Biotechnology Australia Pty Ltd., East Roseville; Monash University, Clayton; St. Vincent's Institute of Medical Research, Eitzroy; Monash Medical Centre, Melbourne, all of Australia

[21] Appl. No.: 336,052

[22] Filed: Apr. 11, 1989

Related U.S. Application Data

[63] Continuation of Ser. No. 741,555, Jun. 5, 1985, abandoned.

[30] Foreign Application Priority Data

Jun. 8, 1984 [AU] Australia .............................. PG5427
Apr. 4, 1985 [AU] Australia .............................. PH00031

[51] Int. Cl.$^5$ .................... C07K 15/14; G01N 33/536
[52] U.S. Cl. ..................................... 436/518; 436/536; 436/543; 436/547; 436/548; 436/817; 530/397; 530/399; 530/412; 530/417; 530/806; 530/850; 530/389.2; 530/388.24
[58] Field of Search ................ 436/518, 536, 543–545, 436/547, 548, 817; 530/387, 397, 399, 806, 808, 850

[56] References Cited

U.S. PATENT DOCUMENTS

| | | | |
|---|---|---|---|
| 3,984,539 | 10/1976 | Khouw et al. | 424/87 |
| 4,624,944 | 11/1986 | Li et al. | 514/12 |
| 4,737,578 | 4/1988 | Evans et al. | 530/350 |
| 4,740,587 | 4/1988 | Ling et al. | 530/313 |
| 4,798,885 | 1/1989 | Mason et al. | 530/350 |

FOREIGN PATENT DOCUMENTS

8606076 10/1986 World Int. Prop. O. .

OTHER PUBLICATIONS

W. J. Herbert, in D. M. Weir (ed.), *Handbook of Experimental Immunology*, 3rd Edition, Blackwell Scientific Publications, 1978, pp. A3.1–A3.15.

(List continued on next page.)

Primary Examiner—David A. Saunders
Attorney, Agent, or Firm—Sandler, Greenblum, & Bernstein

[57] ABSTRACT

A protein which satisfies all the biological criteria which are characteristic of inhibin has been isolated from a gonadal source. The purification and characterization of inhibin and the use of the purified material to raise antibodies, the use of inhibin and said antisera in a quantative radioimmunoassay, and applications in vitro and in vivo of inhibin and antibody to inhibin, are described.

There is provided a purified protein, inhibin, characterised in that
  a. the apparent molecular weight as determined by SDS-PAGE is 56,000±1,000
  b. the isoelectric point is in the range 6.9–7.3
  c. the protein can bind specifically to Concanavalin A-Sepharose
  d. the protein consists of two sub-units, characterized in that
   i. their apparent molecular weights as determined by SDS-PAGE are 44,000±3,000 and 14,000±2,000 respectively.
   ii. the isoelectric point of the 44,000 molecular weight sub-unit is in the range 6.0–7.0
   iii. the N-terminal amino acid sequences of the two sub-units are as described herein
  e. the protein can suppress follicle stimulating hormone (FSH) but not luteinising hormone (LH), thyroid stimulating hormone or prolactin in an in vitro bioassay system
  f. the protein can be labeled with radioactive iodine.

There is also provided a method for isolating and purifying inhibin from mammalian ovarian follicular fluid, characterised by
  a. one or more gel permeation chromatography steps;
  b. one or more reversed-phase high performance liquid chromatography steps;
  c. one or more preparative polyacrylamide gel electrophoresis steps;
  d. Electrophoretic elution of the purified inhibin.

132 Claims, 4 Drawing Sheets

OTHER PUBLICATIONS

Robertson, D. M. et al. "Isolation of Inhibin from Bovine Follicule Fluid," Bio Bioph Res Comm; (126.1 (1985) pp. 220–226.

Miyamoto, K. et al., "Isolates of Porcine Follecular Fluid Inhibin of 32K Daltons", Bio Bioph Res Comm; 129:2 (1985) pp. 396–403.

Ling et al. "Isolation and Partial Characterization of $M_r$ 32000 Protein . . . Follicular Fluid", Proc Natl Acad. Sci 82 (1985) pp. 7217–7221.

Rivier, J. et al., "Purification and Partial Characterization of Inhibin from Porcine Follicular Fluid", *Biochem and Bioph Res Comm* pp. 120–127 (1987).

Mason, A. J. et al., "Complementary DNA Sequence of Ovarian Follicular Fluid Inhibin Show Precursor Stucture and Homology with Transforming Growth Factor-Beta", *Letters to Nature* pp. 659–663. (1985).

Fukuda, M. et al., "Isolation of Bovine Follicular Fluid Inhibin of About 32 KDa", *Molecular and Cellular Endocrinology*, 44: pp. 55–60 (1986).

Mason, A. J. et al. "Structure of Two Human Ovarian Inhibin", *Biochem and Bioph Res Comm*, pp. 957–964 (1986).

Forage, R. G. et al. "Cloning and Sequence Analysis of cDNA Species Coding for the Two Subuits of Bovine Follicular Fluid", Proc. Natl. Acad. Sci. USA pp. 3091–3095 (1986).

McLachlan, R. I. et al., "Plasma Inhibin Levels During Gonadotropin-Induced Ovarian Hyperstimulation of IVF": *The Lancet*, pp. 1233–1234 (1986).

Tsonis, C. G. et al., "Dual Gonodal Control of Follicle Stimulating Hormone", *Nature*, pp. 724–725 (1986).

de Kreiser, D. M. et al., "Control of FSH and LH Secretion", Monograph of Endocrinology pp. 12–43 (1983).

Au, C. L. et al., "Effects of Testosterone on Testicular Inhibin and Fluid Production in Intact and Hypophysectomized Adult Rats", *J. Reprod. Fert.* pp. 257–266 (1986).

Au, C. L. et al., "Relationship Between Testicular Inhibin Content and Serum FSH Concentrations in Rats After Bilateral Efferent Duct Ligation", *J. Reprod. Fert.* pp. 351–356 (1984).

Robertson, D. M. et al., "The Effects of Inhibin Purified from Bovine Follicular Fluid in Several In-Vitro Pituitary Cell Culture Systems", *Molecular and Cellular Endocrinology*, pp. 29–36 (1986).

de Kreiser, D. M. et al., "Fertility Regulation in the Male: Recent Developments", Recent Advances in Fertility Regulation, pp. 112–121 (1980).

de Kreiser, D. M., "Inhibin Becomes a Reality", *Research in Reproduction* pp. 1–4 (1986).

Robertson et al., "The Use of $^{51}$Cr for Assessing Cytoxicity in an In-Vitro Bioassay for Inhibin" Molecular and Cellular Endocrinology pp. 119–127 (1982).

Scott, R. S. et al., "The Specificity of Inhibin Bioassay Using Cultured Pituitary Cells", Molecular and Cellular Endocrinology, pp. 307–316 (1982).

Le Gac, F. et al., "Inhibin Production by Sertoli Cell Cultures," Molecular and Cellular Endocrinology pp. 487–498 (1982).

Baker, H. W. G., "Present Status of Research on Inhibin: An Appraisal", *Clinical Reproduction and Fertility*, pp. 161–174 (1983).

McLachlan, R. I. et al., "The Human Placenta: A Novel Source of Inhibin", Biophys. Biochem. Res. Comm. pp. 51–58 (1986).

de Kreiser, D. M., "The Testis, *Reproduction in Mammals*" pp. 76–90.

de Kreiser, D. M., "Morphology and Physiology of the Testis", Principles and Practice of Endocrinology and Metabolism pp. 928–937.

McLachlan, R. I. et al., "Circulating Immunoactive Inhibin in the Luteal Phase and Early Gestation of Women Undergoing Ovulation Induction", *Fertility and Sterility pp. 001–005 (1987)*.

Biological Abstracts, vol. 79, No. 94–408, 1985.

Chemical Abstracts, vol. 94, No. 187299k, 1981.

Chemical Abstracts, vol. 98, No. 626 g, 1983.

Seidah, N. G., Arbatti, N. J. Rochemont, J. Sheth, A. R., and Chretien, M. Complete Amino Acid Sequence of Human Seminal Plasma Beta-Inhibin, FEBS Letters, 175 (1984), pp. 349–355.

Ross, G. T. and Vande Wiele, R. L., Frantz, A. G., The Ovaries and the Breasts, In: Textbook of Endocrinology (Williams, Ed.) (1981), pp. 355–411.

McLachlan, R. I., Robertson, D. M., Burger, H. G. and de Kretser D. M., The Radioimmunuassay of Bovine and Human Follicular Fluid, and "Serum Inhibin, Molecular and Cellular Endocrinology 46 (1986), pp. 175–185.

(List continued on next page.)

OTHER PUBLICATIONS

Briand, J. P., Muller, S., and Van Regcamortel, M.H.V., Synthetic Peptides as Antigens: Pitfalls of Conjugation Methods, J. Immunol. Methods 78 (1985), pp. 59–69.

de Jong, F. H., Jansen, E. H. J. M., Hermans, W. P., and van der Molen, H. J., Purification, Characterization and Physiological Significance of Inhibin from Ovarian Follicular Fluid. Adv. Biosci. 34 (1982), 73–84.

Sevier, E. D., David, G. S., Martinis, J., Desmond, W. J., Bartholomew, R. M., and Wang, R., Monoclonal Antibodies in Clinical Immunology, Clin. Chem. 27, (1981), pp. 1797–1806.

Dobos, M., Burger, H. G., Hearn, M. T. W., and Morgan, F. J., Isolation of Inhibin From Ovine Follicular Fluid Using Reversed-Phase Liquid Chromatography, Molecular and Cellular Endocrinology 31 (1983), pp. 187–198.

Franchimont, P., Verstraclen-Proyard, J., Hazee-Hargelstein, M. T.: Renard, C., Demoulin, A., Bourguignon, J. P., and Hustin, J., Inhibin: From Concept to Reality, Vitamins and Hormones, 37, (1979), pp. 243–302.

de Jong, F. H. and Robertson, D. M., Inhibin: 1985 Update on Action and Purification, Molecular and Cellular Endocrinology 42 (1985), pp. 95–103.

Astedt, B., Lecander, I., Brodin, T., Lundblad, A., and Low, K., Purification of a Specific Placental Plasminogen Activator Inhibitor by Monoclonal Antibody and Its Complex Formation with Plasminogen Activator, Thrombosis and Haemostasis (1985, pp. 122–125).

Kopitar, M., Rozman, B., Babnik, J., Turk, V., Mullins, D. E., and Wun, T. C., Human Leukocyte Urokinase Inhibitor-Purification Characterization and Comparative Studies Against Different Plasminogen Activators, Thrombosis and Haemostatis 54 (1985) 750–755.

Begent, R. H. I., Green, A. I., Bagshawe, K. D., Jones, B. E. Keep, P. A., Scarle, F. Jewkes, R. F., Barrat, G. M., and Ryman, B. E., Liposomally Entrapped Second Antibody Improves Tumour Imaging with Radiolabelled (First) Antitumour Antibody, The Lancet, 2 (1982), pp. 739–741

Ellouz, F., Adam, A., Clorbaru, R. and Lederer, E. Minimal Structural Requirement for Adjuvant Activity of Bacterial Peptidoglycan Derivatives, Bioch, and Biophys. Res. Comm: 59 (1974), pp. 1317–1322.

Lowry, O. H., Rosebrough, N. J., Farr, A. L., and Randall, R. J., Protein Measurement with the Folin Phenol Reagent, J. Biol. Chem. 193 (1951), pp. 265–275.

Bradford, M. M., A Rapid and Sensitive Method of the Quantitiation of Microgram Quantities of Protein, Utilizing the Principle of Protein Dye Binding, Analytical Biochem 72 (1976), pp. 248–254.

McCullagh, D. R., "Dual Endocrine Activity of the Testes," Science 76 (1932), 19–14 20.

de Jong, F. H., "Inhibin-Fact or Artifact," Molecular and Cellular Endocrinology 13 (1979), pp. 1–10.

Seidah, N. G., Ramasharma, K., Sairam, M., and Chretien, M., "Partial Amino Acid Sequence of a Human Seminal Plasma Peptide with Inhibin-like Activity," PEBS Letters 167 (1984), 98–102.

Sheth, A. R., Aranbatti, N., Carlquist, M., and Jornvall, H., "Characterization of a Polypeptide from Human Seminal Plasma with Inhibin (Inhibition of a FSH Secretion)-like Activity," FEBS Letters 165 (1984), 11–15.

Beksac, M., Khan, S., Eliasson, R., Skakkelback, N., Sheth, A., and Diczlalusy, E., "Evidence for the Prostatic Origin of Immunoreactive Inhibin-like Material in Human Seminal Plasma," International Journal of Andrology 7 (1984), 389–397.

Lilja, H. and Jeppsson, J. O., "Amino Acid Sequence of the Predominant Basic Protein in Human Seminal Plasma," FEBS Letters 182 (1985), 181–184.

Laemmli, U. K., "Cleavage of Structural Proteins During the Assembly of the Head of Bacteriophage T4, Nature 227 (1970), 680–685.

Scott, R. S., Burger, H. G., and Quigg, H., "A Simple and Rapid In Vitro Bioassay for Inhibin", Endocrinology 107 (1980), 1536–1542.

Au, C. L., Robertson, D. M., and de Kretser, D. M., "In Vitro Bioassay of Inhibin in Testes of Normal and Cryptorchid Rats," Endocrinology 112 (1982), 239–244.

Reid, M. S., and Bieleski, R. L., "A Simple Apparatus for Vertical Flat-Sheet Polyacrylamide Gel Electrophoresis", Analytical Biochemistry 22 (1968), 374–381.

Hunkapiller, M. W., and Hood, L. E., "Analysis of Phenylthiohydantoins by Ultrasensitive Gradient High Performance Liquid Chromatography," Methods in Enzymology 91 (1983), 486–493.

(List continued on next page.)

OTHER PUBLICATIONS

O'Farrell, P., "High Resolution Two-Dimensional Electrophoresis," J. Biol. Chem. 250 (1975), 4007–4021.

Vaitukaitas, J., Robbins, J. B., Nieschlag, E., Ross, G. T., "A Method of Producing Specific Antisera with Small Doses of Immunogen", Journal of Clinical Endocrinology and Metabolism 33 (1971), pp. 988–991.

Bolton, A. E., and Hunter, W. M., "The Labelling of Proteins to High Specific Radioactivities by Conjugation to a 125 I-Containing Acylating Agent", Biochem J. 133 (1973), 529–539.

Peterson, M. A., and Swerdloff, R. S., "Separation of Bound From Free Hormone in Radioimmunoassay of Lutropin and Follitropin," Clin. Chem. 25 (1979), 1239–1241.

Mougdal, N., Murthy, H. M. S., Murthy, G. S., and Rao, A. J., "Regulation of FSH Secretion in the Primate by Inhibin: Studies in the Bonnet Monkey (M. radiata) Gonadal Proteins and Peptides and Their Biological Significance (Sairam, ed.), World Scientific Publishing, Singapore (1984), 21–37.

Henderson, K. M., Franchimont, P., Lecomte-Yerna, M. J. Hudson, N., and Ball, K., "Increase in Ovulation Rate After Active Immunization of Sheep with Inhibin Partially Purified from Bovine Follicular Fluid," J. Endocrinology 102 (1984), 305–309.

Cummins, L. O'Shea, T., Bindon, B. M., Proc. Aust. Soc. Reprod. Biol. (1983), 81.

Al. Obaidi, Bindon, B. M., O'Shea, T., Hillard, M. A., Cheers, M., Proc. Aust. Soc. Reprod. Biol. 15 (1983), 80.

Gemzell, C., "Induction of Ovulation with Human Gonadotropins," Recent Prog. Hormone Research 21 (1965), 179–204.

Bardin and Paulsen, "The Testes," Textbook of Endocrinology (Williams, ed.) (1981), 293–354.

Cummins, L., Ph.d Thesis (1983), University of New England, Armidale, Australia, pp. 160–166.

Sheth, A. R., Sheth, P. R., Roy, R., Interaction of Thyrotrophin Releasing Hormone with Inhibin in Male Rats, Journal of Endocrinology 98 (1983), pp. 1–6.

Merril, C. R., Foldman, D., Sedman, S. A., Ebert, M. H., Ultrasensitive Stain for Proteins in Polyacrylamide Gels Shows Regional Variation in Cerebrospinal Fluid Proteins, Science 211 (1981), pp. 1437–1438.

Chari, S., Duraiswami, S., Daume, E., Sturm, G., Biological Characteristics of Inhibin from Human Ovarian Follicular Fluid, Int. Cong. Ser. Excerta Med. 551 (1981), pp. 463–467.

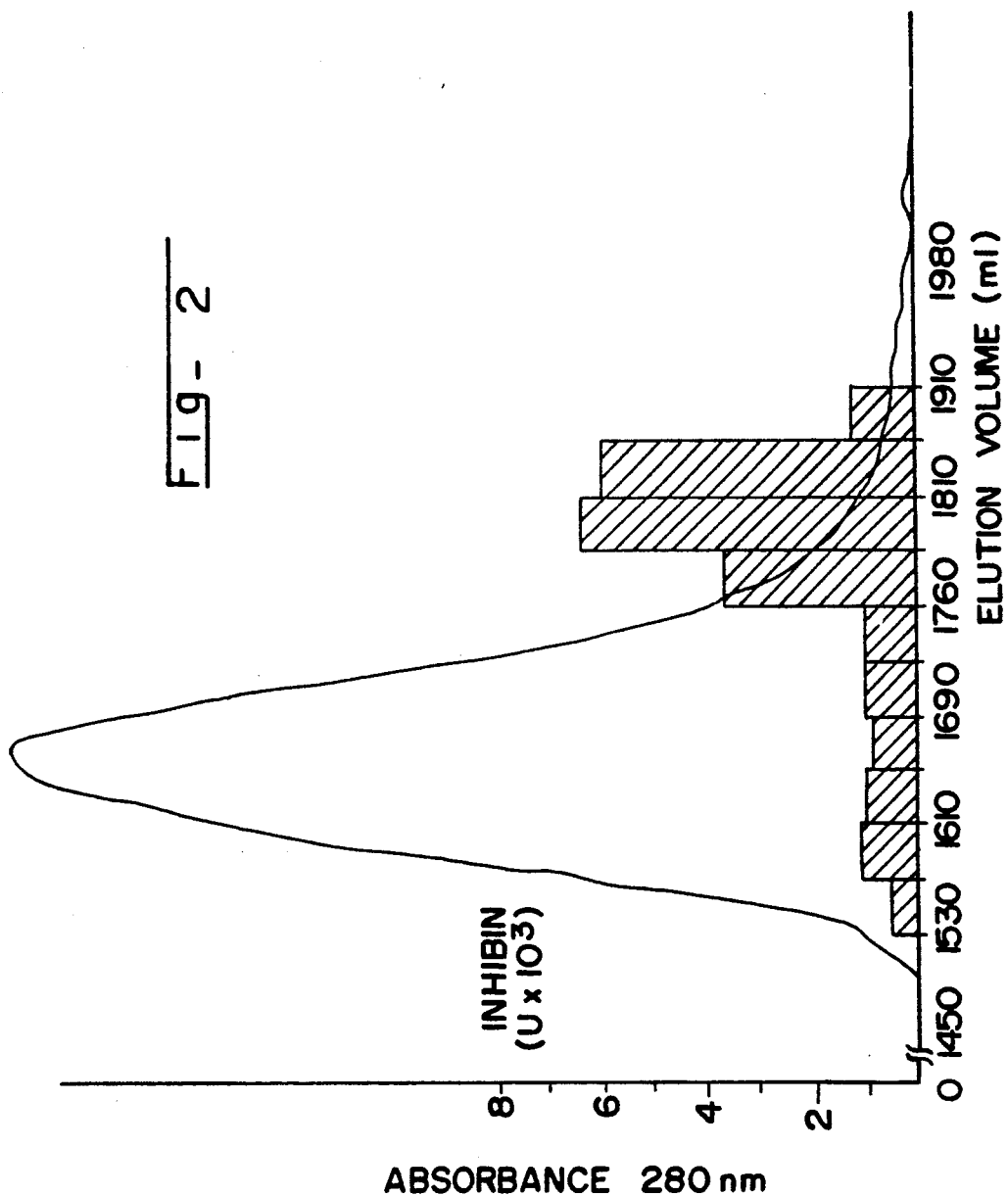

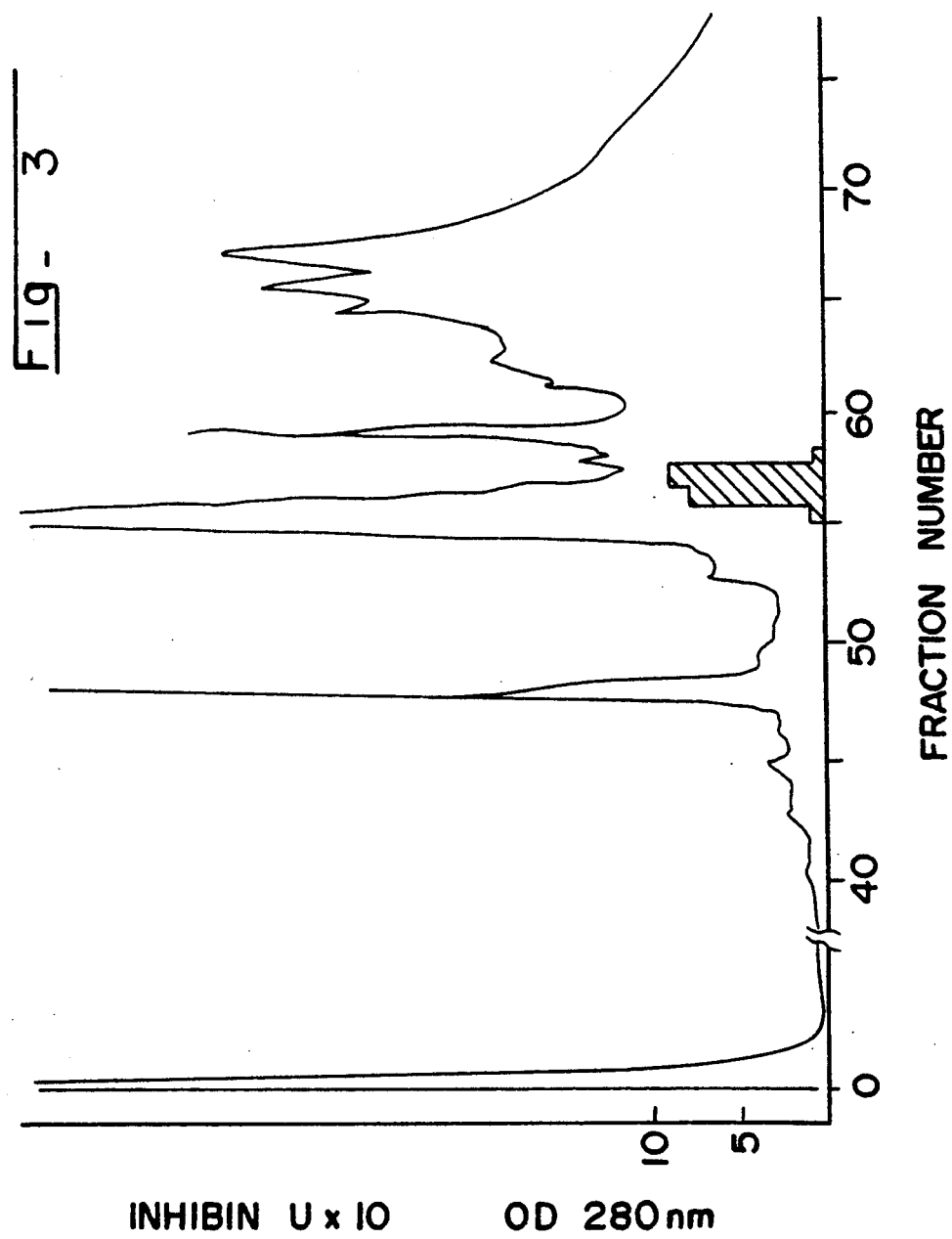

INHIBIN ISOLATED FROM OVARIAN FOLLICULAR FLUID

This is a continuation of application Ser. No. 741,555 filed June 5, 1985 and now abandoned.

This invention relates to the isolation of a biologically active factor from mammalian ovarian follicular fluid, and valuable uses of that factor.

On the basis of circumstantial evidence and limited experimentation it was suggested as early as 1932 that the gonads produced a non-steroidal factor, termed inhibin, which was capable of selectively suppressing the pituitary gland secretion of follicle stimulating hormone (FSH) (McCullagh, Science 76, (1932) 19). Since that time the development of radioimmunoassays to measure FSH has led to the accumulation of a substantial body of evidence to suggest that inhibin exists, but it was not until the early 1970's that any attempt to isolate and identify this substance was made. Since that time a number of groups of investigators have attempted to purify inhibin from a several gonadal sources with conflicting results (de Jong, Mol. Cell. Endocrinol. 13, (1979) 1). Some investigators have claimed to have isolated and sequenced inhibin from human seminal plasma, with the molecular weights of their species of inhibin being 5,000 and 14,000 daltons (Seidah et al., FEBS Letters 167, (1984) 98; Sheth et al., FEBS Letters, 165, (1984) 11). Furthermore, the gonadal origin of these material has been seriously questioned (Beksac et al., Int. J. Andrology 7, (1984) 389; Lilja and Jeppsson, FEBS Letters 182, (1985) 181). Other groups of investigators have utilized fluid collected from the seminiferous tubules of the testis (rete testis fluid) and also ovarian follicular fluid to attempt to isolate gonadal inhibin. As yet these attempts, despite being carried out over a period of 12 years, have been unsuccessful in obtaining a purified material. This background indicates that there is no general agreement as to the nature, chemical features or site of production of the substance defined as inhibin.

The properties of bovine follicular fluid extracts have led to the postulate that there is a substance or substances, "inhibin", with specific functions. We have now isolated a material from a gonadal source which satisfies all the biological criteria which are characteristic of inhibin.

The present invention relates to the purification and characterization of inhibin and to the use of the purified material to raise antibodies, the use of inhibin and said antisera in a quantative radioimmunoassay, and applications in vitro and in vivo of inhibin and antibody to inhibin.

According to one aspect of the present invention there is provided a purified protein, inhibin, characterized in that
  a) the apparent molecular weight as determined by SDS-PAGE is 56,000±1,000
  b) the isoelectric point is in the range 6.9–7.3
  c) the protein can bind specifically to Concanavalin A-Sepharose
  d) the protein consists of two sub-units, characterized in that
     (i) their apparent molecular weights as determined by SDS-PAGE are 44,000±3,000 and 14,000±2,000 respectively
     (ii) the isoelectric point of the 44,000 molecular weight sub-unit is in the range 6.0–7.0
     (iii) the N-terminal amino acid sequences of the two sub-units are as described hereinbelow
  e) the protein can suppress follicle stimulating hormone (FSH) but not luteinising hormone (LH), thyroid stimulating hormone or prolactin in an in vitro bioassay system
  f) the protein can be labeled with radioactive iodine.

According to another aspect of the invention, there is provided a method for isolating and purifying inhibin from mammalian ovarian follicular fluid, characterized by the following steps:
  a) one or more gel permeation chromatography steps;
  b) one or more reversed-phase high performance liquid chromatography steps;
  c) one or more preparative polyacrylamide gel electrophoresis steps;
  d) Electrophoretic elution of the purified inhibin.

Preferably the gel permeation chromatography step is carried out using a gel permeation support with high pore volume, for example Sephacryl S200 or Sephadex G100 (both Sephacryl and Sephadex are trade marks of Pharmacia). Preferred elution methods utilize volatile solvents containing, for example, ammonium acetate, acetic acid, or similar compounds, to allow direct recovery of biological activity by lyophilization or vacuum drying.

Preferably the reversed-phase high-performance liquid chromatography is carried out using chemically-bonded N-alkylsilica column packings of narrow particle size distribution, most suitably 5–10μ. The eluents used may be volatile or non-volatile, and contain ionic modifiers such as trifluoroacetic acid (TFA), ammonium bicarbonate, ammonium acetate, or sodium phosphate, in a gradient of water with a miscible organic solvent such as methanol, acetonitrile, or isopropanol. A preferred procedure utilizes a gradient of 0–50% acetonitrile in 0.1% TFA. Various preparative polyacrylamide gel electrophoresis (PAGE) methods can be employed in the presence of sodium dodecyl sulphate (SDS) using PAGE gels of various porosities and cross-linking content. A preferred buffer system for electrophoresis is based on the method of Laemmli, as described in Nature 227, (1970) 680.

There is further provided a method for raising specific antibodies to the inhibin, said antibodies having the ability to neutralize the activity of inhibin in the in vitro bioassay, and to cause an increase in gonadal weight in vivo.

There is still further provided a method for the radioimmunoassay of inhibin which can be used for the measurement of inhibin in biological samples such as plasma, serum or urine.

One embodiment of the present invention will now be described in detail by way of example only with reference to the following non-limiting examples, and the accompanying drawings in which:

FIG. 2 shows the elution profile of inhibin activity in bFF fractionated on Sephadex G100.

FIG. 3 shows the elution profile of inhibin activity in bFF fractionated by reversed-phase high performance liquid chromatography (RP-HPLC) after prior gel chromatography.

Abbreviations used herein are as follows:

| | |
|---|---|
| bFF | bovine ovarian follicular fluid |
| RP-HPLC | reversed-phase high performance liquid chromatography |
| PAGE | polyacrylamide gel electrophoresis |
| FSH | follicle stimulating hormone |
| LH | luteinising hormone |
| U | units |
| GF | gel filtration |
| kD | kilo Daltons |
| TFA | trifluoroacetic acid |
| SDS | sodium dodecyl sulphate |

EXAMPLE 1

Purification of inhibin from bovine ovarian follicular fluid

The purification procedure is based on the sequential application of one or more gel permeation steps, one or more reversed phase high resolution chromatography steps and one or more PAGE steps.

Collection of bovine follicular fluid (bFF)

Bovine ovaries were obtained from local abattoirs and bFF aspirated into a chilled vessel containing the protease inhibitors Trasylol (10 U/ml) and phenylmethylsulphonyl fluoride (24 μg/ml). The bFF was stored frozen at −20° C.

The procedure for purification of inhibin consisted of 4 stages or steps. In the sections below an outline of the procedure is described and details of the purification procedure are presented.

The steps in the purifications procedure are as follows:

(A) Gel permeation chromatography on Sephacryl S-200.
(B) Gel permeation chromatography on Sephadex G-100.
(C) Reversed phase high performance liquid chromatography.
(D) Preparative polyacrylamide gel electrophoresis.
(E) Electrophoretic elution of samples.

The purification of inhibin was monitored by the bioassay method of Scott et al. (Endocrinology 107, (1980) 1536), used with minor modifications (Au et al., Endocrinology 112, (1983) 239). The method is based on the ability of inhibin to cause dose-dependent reduction of FSH but not LH cellular content of rat anterior pituitary cells in culture.

Step A

Figure 1:
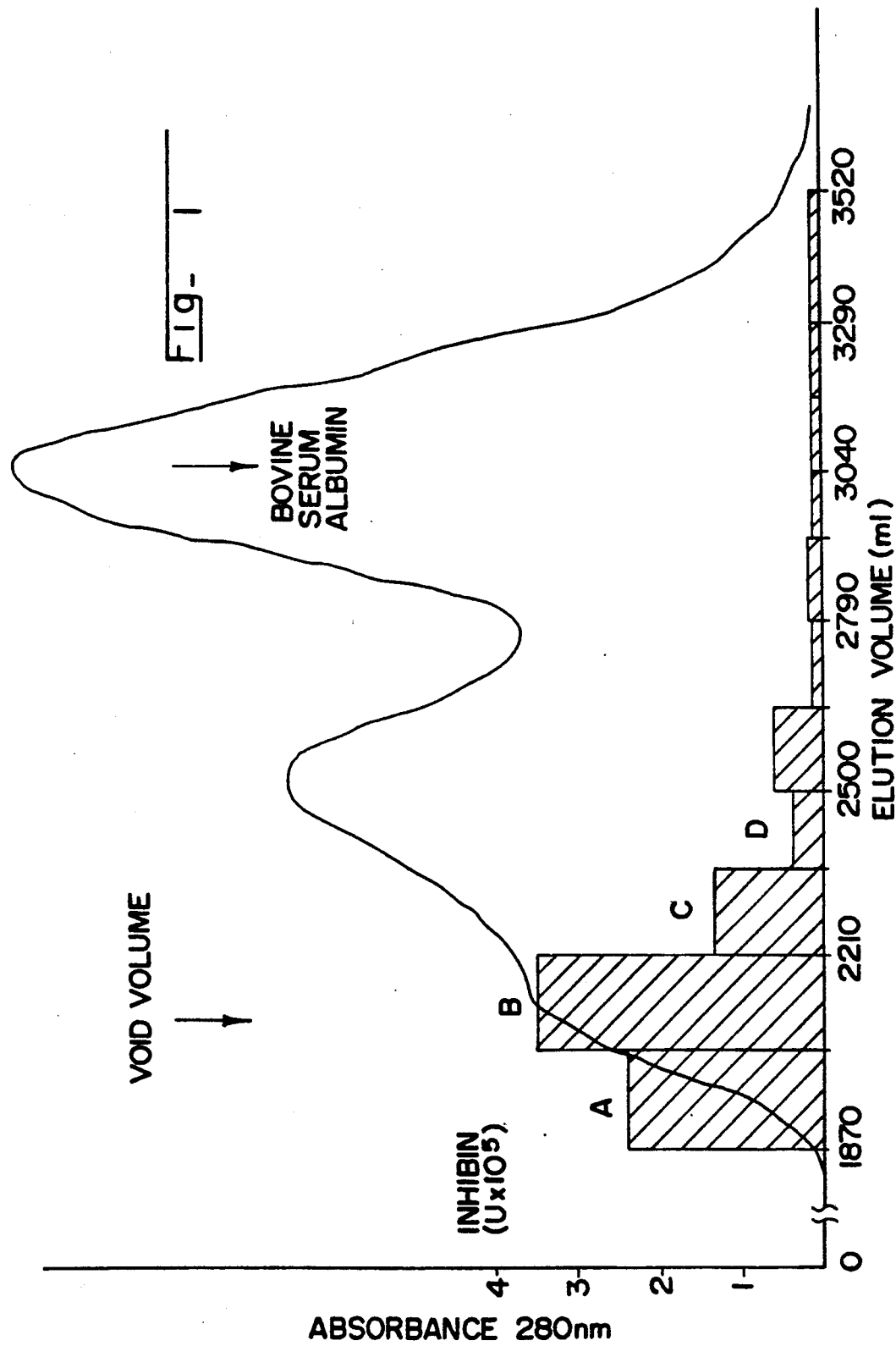
FIG. 1 shows the elution profile of inhibin activity in bovine ovarian follicular fluid (bFF) fractionated on Sephacryl S-200.

Gel Permeation Chromatography on Sephacryl S200: Elution Buffer 0.05M Ammonium Acetate pH 7.0 bFF (50-100 ml) was diluted with 0.05M ammonium acetate pH 7.0 (25-50 ml) and centrifuged (12000 g×30 min at 4° C.). The supernatant (75-150 ml) was fractionated on a Sephacryl S200 gel filtration column (9×90 cm) at a flow rate of 70-100 ml per hour. As seen in FIG. 1, inhibin activity was located in a void volume region (MW≧90,000) of this column. 90% recoveries of inhibin activity were obtained with a 3-4 fold increase in specific activity.

Step B

Gel Permeation Chromatography on Sephadex G100: Elution Buffer 4M Acetic Acid

Void volume fractions (A, B, C and D, FIG. 1) were combined and 25-50% of the pooled fractions were acidified with glacial acetic acid (chromogen-free) to a final concentration of 4M acetic acid and kept at 4° C. for one hour. The remaining 50-75% was stored frozen at −20° C. prior to subsequent fractionation. The acidified pool (approximately 120 ml) was applied to a Sephadex G100 gel filtration column (9×90 cm) with 4M acetic acid as eluting buffer at a flow rate of 70-100 ml per hour. All operations with both gel filtration columns were performed at 4° C. Under these conditions the bulk of the inhibin activity eluted in a lower molecular weight region (elution volume 1760-1880 ml, MW range 20,000-60,000, FIG. 2) with a 10-20 fold increase in specific activity and 45% recovery of inhibin activity in this region. Using analytical columns (e.g., 2.5×100 cm) similar profiles of activity with higher specific activities (10-50 fold) have been observed.

Step C

Reversed Phase High Performance Liquid Chromatography (RP-HPLC)

The column fractions (elution volume approximately 1760-1910 ml) from Step B were pooled prior to loading onto the RP-HPLC column. The column employed was an Ultrapore RPSC (Beckman, Berkeley, Calif.). The mobile phase used was a linear gradient between 0.1% TFA in water and 50% acetonitrile in 0.1% TFA; the flow rate was 1 ml/per minute and 0.5 ml fractions were collected. Three loading procedures were employed: (a) the sample was lyophilised and 1 mg dissolved in 4M acetic acid to a concentration of 8-10 mg dry weight/ml, centrifuged in approximately 100 μl 4M acetic acid and applied to the HPLC column via the injector; (b) the lyophilised material (5-10 mg) was dissolved in 20 ml of 4M acetic acid, centrifuged and loaded onto the column via a solvent port on the HPLC; (c) the unlyophilised material (approximately 100 ml) was filtered through a 0.5 μm filter (FH; Millipore Corp) prior to loading via a solvent port on the column at a flow rate of 2 ml/minute.

The inhibin regions from the bulk runs (b) and (c) were rechromatographed. Each fraction was combined with the contents of the corresponding tubes from the repeat runs (if required) and aliquots were taken for bioassay, amino acid analysis and SDS-PAGE. The acetonitrile from each fraction was then removed by evaporation under $N_2$ and the sample lyophilised. As seen in FIG. 3, inhibin activity was found in one region of the chromatogram, corresponding to approximately 30% acetonitrile. The sample load in this experiment was 1 mg.

Recoveries of inhibin of 40% were obtained with the various loading procedures, although the HPLC column performance was markedly influenced by the latter two procedures. A 10-fold increase in specific activity was attained with this HPLC step, with an overall 160-fold increase in specific activity.

Step D

Preparative Polyacrylamide Gel Electrophoresis

The inhibin-containing fractions obtained by RP-HPLC were dissolved in non-reducing sample buffer (0.06M Tris-HCl pH 6.8, 12.5% glycerol, 1.25% w/v SDS and 0.006% bromophenol blue) and fractionated on a vertical polyacrylamide gel electrophoresis apparatus (Reid and Bieleski, Analytical Biochemistry, 22, (1968) 374) with modifications. The SDS polyacrylamide gel electrophoresis solutions (Laemmli, Nature 227 (1970) 680) consisted of a stacking gel (0.125M Tris-HCl pH 6.8, 0.1% w/v SDS, 5% acrylamide, 0.13% Bis acrylamide, 0.1% ammonium persulphate) and a separating gel (0.38M Tris-HCl pH 8.8, 0.1% w/v SDS, 7.5% acrylamide, 0.2% Bis acrylamide, 0.03% ammonium persulphate). The electrophoretic buffer was 2.5 mM Tris-glycine buffer containing 0.05% (w/v) SDS. The protein load (500–700 μg) was divided between the eight sample slots.

The gels were electrophoresed initially at 20 mA until the sample had migrated into the separating gel (1.5h), then the current was increased to 30mA for the duration of the run (4h) until the bromophenol blue marker reached the bottom of the gel. The gel was stained with 0.5% Coomassie blue in acetic acid: isopropyl alcohol:water 1:3:6 v/v (15 min) and destained with acetic acid: methanol:water, 50:165:785 v/v, and the inhibin region (molecular weight approximately 56,000) which was visualised by this procedure was sectioned into 2 mm slices using a scalpel and ruler. Gel slices above and below the inhibin region were also taken. The gel slices were stored in sealed tubes at $-15°$ to $-20°$ C. prior to electrophoretic elution.

Figure 4A:
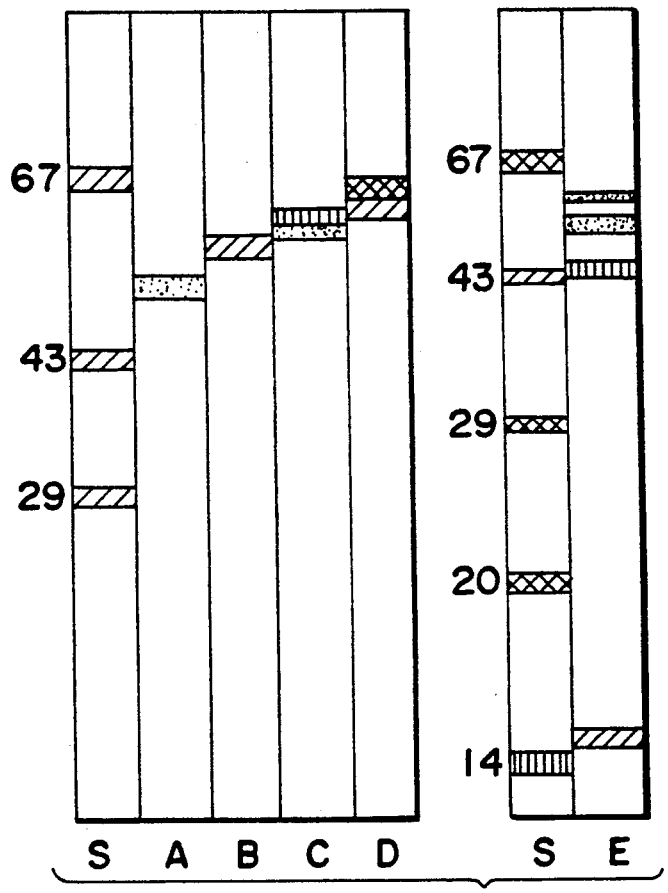
FIG. 4A shows reduced and non-reduced SDS-polyacrylamide gel electrophoretic patterns of four sequential fractions obtained by preparative PAGE.
Figure 4B:
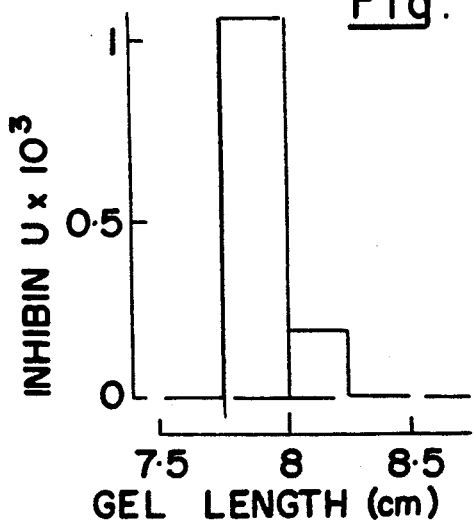
FIG. 4B shows the concentration of inhibin along the length of the gel.

FIG. 4 shows reduced and non-reduced SDS-gel electrophoretic patterns of 4 sequential fractions (A, B, C and D) obtained by preparative PAGE purification. Inhibin activity was located primarily in fraction B (apparent molecular weight 56,000±1,000 mean±SD; 5 purified inhibin preparations). Under reducing conditions, fraction B reduced into two major bands with apparent molecular weights of 44,000 ±3,000 and 14,000±2,000 (n=5) (Lane E). The Laemmli (1970) SDS-PAGE system was employed. Proteins were localized by silver staining. Protein standards used were: bovine serum albumin (molecular weight 67,000); ovalbumin (43,000); carbonic anhydrase (29,000); goose lysozyme (21,000); hen egg lysozyme (14,500). The reductant was 0.1% 2-mercaptoethanol.

Step E

Electrophoretic Elution at Room Temperature

The method used was modified from that of Hunkapiller et al. (Methods in Enzymology, 91 (1983) 227). Gel slices were diced in distilled water with a razor blade, washed in elution buffer (0.1% SDS in 0.05M $NH_4HCO_3$) for 5 min and placed in an electrophoretic elution cell fitted with dialysis membrane discs (6,000–8,000 molecular weight cut off). The gel slices were covered with soaking buffer (2% SDS in 0.4M $NH_4HCO_3$), and overlayed with elution buffer (0.1% SDS in 0.05M $NH_4HCO_3$) Solid sodium thioglycollate, to a final concentration of 0.5 mM, was added to the elution buffer. Gel pieces were allowed to soak for 3–5 hr prior to the initiation of the electrophoretic elution process at 50 V (direct current). After 12–16 hr the elution buffer was replaced with dialysis buffer (0.02% SDS in 0.01M NH ) followed by further electrophoretic elution at 80 V (direct current) for 20–24 hr until the Coomassie blue stain and protein had migrated into the sample collection well. The eluted sample was removed from the collection well by means of a bent-tipped 50 μl Hamilton syringe, aliquoted and either frozen or lyophilised. Samples of the purified fractions were set aside for the in vitro bioassay, amino acid analysis and molecular weight determination using SDS-PAGE as employed with the silver staining technique.

Using purification procedures based on the above methods, i.e. a combination of gel permeation chromatography, RP-HPLC and preparative PAGE, inhibin activity was recovered as a single protein band on SDS-PAGE (FIG. 4), with an apparent molecular weight of 56,000±1,000 (5 preparations).

The purified preparations of inhibin suppress FSH but not luteinising hormone, thyroid stimulating hormone or prolactin in the in vitro bioassay, indicating that the purified product is specific in suppressing FSH. The suppression is not due to non-specific toxic effects.

EXAMPLE 2

Alternative Purification Procedures

Inhibin was isolated as in Example 1, except that inhibin was precipitated by adjusting the pH of the void volume fraction from Step A to pH 4.75 with 4M acetic acid and centrifuged at 12,000×g for 30 min at 4° C. The resulting pellet was dissolved in 0.05M ammonium acetate pH 7.0. The solubilization of the pellet was aided by homogenization and sonication in buffer at room temperature. The sample was adjusted to 4M acetic acid with glacial acetic acid and centrifuged prior to application to the column for the second gel permeation step (Step.B). The overall recoveries of inhibin activity including pH precipitation and acidification of the dissolved pellet was 34%. The modification has the advantage that the column sample volume is reduced by 75% allowing a greater throughput of material. Inhibin activity was recovered in similar column fractions (elution volumes 1700–2100 ml) to that in the procedure of Example 1 following fractionation by gel filtration with 4M acetic acid as elution buffer. The subsequent behaviour of inhibin on the RP-HPLC and the PREP-PAGE procedure was not influenced by the various modifications examined in this example.

EXAMPLE 3

Further Chemical Characterization of Inhibin

Analytical SDS-PAGE of the final product under non-reducing conditions gave a single band with an apparent molecular weight of 56,000±1,000 (mean±SD, 5 preparations) while under reducing conditions two major bands with apparent molecular weights of 44,000±3,000 and 14,000±2,000 (5 preparations) were observed. Evidence of heterogeneity was observed as assessed from electrophoresis of the 56 kD band under non-reducing conditions and the 44 kD band under reducing conditions. The apparent molecular weight range for the 56 kD material was between 54,000 and 57,000 while the 44 kD material ranged from 42,000 to 46,000. A single band was observed with the 14 kD band. These findings are consistent with the glycoprotein nature of this molecule.

The pI values of intact inhibin and the larger sub-unit were determined using the 2 dimensional PAGE system of O'Farrell, P. H., J. Biol. Chem, 250 (1975), 4007–4021. Intact inhibin was detected by silver stain and showed a single band with an apparent molecular weight of 56,000 but with several closely associated spots with pI values in the pH range 6.9–7.3. These data are suggestive of a glycoprotein preparation. The 44,000 molecular weight sub-unit showed a single band with an apparent molecular weight of 46,000 with several closely associated spots with pI values in the pH range 6.0–7.0, suggesting that this sub-unit is a glycoprotein.

Further evidence that inhibin is a glycoprotein was established by:

(a) The ability of radiolabelled inhibin to bind to the lectin Concanavalin A immobilized on Sepharose (Trade Mark of Pharmacia, Uppsala, Sweden). From several experiments 15–17% of the tracer bound to the lectin and was released following elution with the sugar methyl-α-D-glucopyranoside (Calbiochem, San Diego, USA).

(b) Binding of horseradish peroxidase-labelled wheat germ lectin to inhibin, following fractionation of inhibin on SDS-PAGE and electrotransfer of the protein on to nitrocellulose. The binding of the lectin was monitored by the intensity of the peroxidase colour reaction. Lectin binding was associated with the 56 kD intact protein and with the 44 kD sub-unit.

EXAMPLE 4

The N-Terminal Amino Acid Sequence of the Two Sub-Units of Inhibin

A purified preparation of inhibin was reduced and carboxymethylated and the two sub-units, of apparent molecular weight 44,000 and 14,000 respectively, were separated by PAGE and recovered from the gel by an electroelution process as described in Step E, Example 1 above. The SDS was removed by methanol precipitation of inhibin, and the N-terminal amino acid sequence determined.

The sequences of the two sub-units are:

| Residue | 44 kD Sub-Unit | 14 kD Sub-Unit |
| --- | --- | --- |
| 1 | xxx | Tyr |
| 2 | Ala | Leu |
| 3 | Val | Glu |
| 4 | Gly | yyy |
| 5 | Gly | Asp |
| 6 | Phe | Gly |
| 7 | Met | Lys |
| 8 | Arg | Val |
| 9 | Arg | Asx |
| 10 | Gly | Ile |
| 11 | Ser | Gln |
| 12 | Glu | yyy |
| 13 | Pro | Lys |
| 14 | Glu | Lys |
| 15 | Asp | |
| 16 | Gln | | xxx = ambiguous
yyy = unable to be determined - insufficient material in these experiments
Asx = Asn or Asp

EXAMPLE 5

Raising of Antibodies to Purified Inhibin

19 μg of inhibin purified as described above was dissolved in 600 μl of Dulbecco's Phosphate Buffer pH 7.4 and emulsified with an equal volume of an oil-based adjuvant (for example, Marcol 52: Montanide 888 in the ratio 9:1. Marcol 52 is a Trade Mark of Esso, and Montanide 888 is a Trade Mark of S.E.P.P.I.C., Paris). Two hundred μl was injected into each of four intramuscular sites and 200 μl injected subcutaneously into a rabbit. The animal was boosted six weeks later with 18 μg of purified inhibin, using the same injection procedure as above. The titre of antibody in the rabbit serum was assessed by its ability to bind to iodinated inhibin (for details see below), or by its ability to neutralize inhibin activity in vitro. The highest titre was observed two weeks post booster (week 8 sample), returning to preimmunization levels by 17–18 weeks.

During immunization, the rabbit increased its testicular volume from 3.0 to 3.5 ml, indicating that immunization against inhibin can increase gonadal weight, presumably by neutralization of endogenous inhibin, thus allowing FSH levels to rise.

EXAMPLE 6

Antiserum Characterization

The week 8 antiserum from the rabbit, prepared as described above, was investigated for its ability to neutralize inhibin activity in vitro. A charcoal-treated bovine follicular fluid preparation was used as inhibin standard in an inhibin in vitro bioassay (Scott et al, Endocrinology, 107, 1980, 1536). It was found that 2 μl of antiserum was sufficient to neutralize a dose of inhibin (2 units) known to give a maximal response in the assay. This neutralizing activity was not present in preimmunization serum. One other rabbit was immunized initially with a less pure inhibin preparation (340μg obtained after the RP-HPLC purification step) and boosted with 22μg of pure inhibin. The initial immunizing injection was in complete Freund's adjuvant, using the immunizing method of Vaitukaitas et al (Journal of Clinical Endocrinology and Metabolism, 33, 1971, 988), while the booster injection procedure was the same cited above. Antiserum (week 9) from this animal also showed neutralizing capabilities in vitro.

EXAMPLE 7

Radioimmunoassay of bFF Inhibin

Purified preparations of inhibin were iodinated either by a mild chloramine-T procedure or by using the Bolton-Hunter reagent (Bolton and Hunter, Biochem J. 133 (1973) 529) to a specific activity of 0.5 μCi/μg as determined by a self displacement procedure in the radioimmunoassay method described below. The iodinated material showed the same apparent molecular weight as the non-iodinated molecule as assessed by SDS-PAGE under reducing and non-reducing conditions. Using the iodinated tracer, a radioimmunoassay procedure was derived using a polyethylene glycol-facilitated second antibody precipitation step to separate antibody-bound and -unbound iodinated hormone (Peterson, M. A. and Swerdloff, R. S.: Clin. Chem. 25 (1979) 1239–1241). Characteristic displacement curves were obtained for purified and for unfractionated bFF preparations. The dose response curve for the purified material showed a sensitivity ($ED_{10}$) of 2 ng/tube with $ED_{50}$ of 25 ng/tube. The dissociation constant of the inhibin-antibody interaction was $4.5 \times 10^{-10}$M at 20° C.

EXAMPLE 8

Inhibition of ovulation in human chorionic gonadotrophin-stimulated 5-day pregnant mice Crude extracts of bovine follicular fluid have previously been shown to inhibit ovulation. The inhibition can be competitively reversed with FSH (L. Cummins, Ph. D. Thesis, 1983, University of New England (Armidale)).

5-7 day pregnant mice were given 1.5 µg inhibin subcutaneously at 9 a.m., followed by subcutaneous injection of 10 IU of HCG at 6:00 p.m. The following morning the number of ova in the ampulla of the Fallopian tube was counted. Inhibin administration significantly inhibited ovulation, as shown in Table 1.

TABLE 1

| Sample | Number of Animals | Number of Ova in Ampulla |
|---|---|---|
| Control (Solvent alone) | 11 | 4.91 ± 2.66 |
| Purified Inhibin* | 7 | 2.43 ± 2.22 |
| bFF** (50 µl) | 8 | 3.38 ± 1.80 |
| bFF (100 µl) | 4 | 2.0 ± 0.0 |

*Inhibin preparation is 75% pure based on intensity of silver stain on SDS-PAGE. The contaminants consist of higher molecular weight material (M.wt 65–70 kD) which is biologically inactive in the inhibin in vitro bioassay. Dose approximately 1.5 µg protein/animal.
**Containing 20 µg/ml inhibin based on inhibin in vitro bioassay.

Purified inhibin and 100 µl bFF both resulted in significant inhibition of ovulation compared to the control ($p<0.01$ and $p<0.05$ respectively by Wilcoxon's test).

EXAMPLE 9

Effect of Immunization on Plasma FSH Levels

In Example 5 above, one rabbit was immunized, and boosted on two further occasions with purified inhibin. The antiserum so obtained neutralized inhibin activity in the in vitro bioassay. It would be expected that in vivo, the antiserum would neutralize circulating inhibin, leading to an elevation of circulating FSH. The rabbit's plasma FSH showed a rise and, fall in concert with the titre of the inhibin antibody in the rabbit serum. The results are shown in Table 2.

TABLE 2

| Weeks Post Booster Injection | Number of Serum Samples | Antibody Titre* | Plasma FSH ng/ml |
|---|---|---|---|
| 3-6, 17, 21 | 6 | ≦0.25 | 4.87 ± 0.76$^a$ |
| 11-14 | 3 | 0.67 ± 0.19 | 5.44 ± 0.24$^b$ |
| 7-10 | 3 | 2.13 ± 0.45 | 6.15 ± 0.44$^c$ |

*Reciprocal of antiserum volume (µl) required to neutralise 1.5 U inhibin in the inhibin in vitro bioassay.
a vs c; a vs b and c; $p < 0.05$

EXAMPLE 10

Suppression of circulating FSH following acute administration of inhibin to castrated male rats It is expected that purified inhibin, as seen in the experiment below with bovine follicular fluid, should suppress circulating FSH within 4–8 hours of administration. Inhibin (bovine follicular fluid) was administered via the jugular vein into the circulation of 34-day old male rats which had been castrated 3 days earlier, and the levels of plasma FSH 5 hours later were determined by FSH radioimmunoassay.

There was a significant dose-dependent decrease in FSH associated with increasing doses of bovine follicular fluid. Results are shown in Table 3.

TABLE 3

| Sample | Number of Animals | Plasma Expressed as % of Pre-injection levels |
|---|---|---|
| Control (solvent alone) | 5 | 99.3 ± 12.8$^a$ |
| bFF* (62.5 µl) | 5 | 80.8 ± 5.5$^b$ |
| bFF (125 µl) | 5 | 66.6 ± 10.3$^c$ |
| bFF (250 µl) | 5 | 51.9 ± 7.0$^d$ |

*containing 20 µg/ml inhibin based on inhibin in vitro bioassay
a vs b; b vs c; c vs d
p 0.05

EXAMPLE 11

Purification of Inhibin From Ovine Follicular Fluid

We have found that inhibin activity from ovine follicular fluid is purified in a similar manner to bFF inhibin using purifications steps A, B and C above. Its characteristics following steps D and E are similar to those of bFF inhibin. By extension it is expected that purification steps A to E would be applicable to other mammalian inhibins including that from human.

The present invention also relates to inhibin analogues, derivatives, fragments and subunits thereof.

Since FSH is important in the stimulation of ovarian and testicular function, the main potential applications of purified inhibin lie in its ability to specifically inhibit FSH secretion, or in its use as an antigen such that immunization against inhibin will elicit antibodies capable of neutralizing endogenously - occurring inhibin, thereby raising FSH levels. Many studies have been performed in vivo using crude or partially purified extracts of gonadal tissues or fluids in attempts to study the action and physiology of inhibin. In these experiments, effects attributed to but not proven to be due to inhibin or antibodies against inhibin include:

1. Inhibition of gonadal function (Moudgal et al., 1985 in Gonadal Proteins and Peptides and their Biological Significance (ed. Sairam), World Scientific Publishing, Singapore (in press).
2. An increase in ovulation rate (Henderson et al., J. Endocrinol. 102, (1984) 305; Cummins et. al., Proc. Aust. Soc. Reprod. Biol. 15 (1983) 81).
3. An advancement of the onset of puberty (Al Obaidi et al., Proc. Aust. Soc. Reprod. Biol., 15 (1983) 80).

The known properties of inhibin and of FSH suggest a number of possible applications for the purified inhibin and antibody to inhibin according to the present invention:

(i) Increase of ovulation rate: It is recognized that FSH stimulates the development of ova in mammalian ovaries (Ross et. al., (1981) in Textbook of Endocrinology, ed. Williams, p. 355) and that excessive stimulation of the ovaries with FSH will lead to multiple ovulations (Gemzell, Induction of ovulation with human gonadotrophins, Recent Prog. Hormone Res. 21 (1965) 179). We have demonstrated that inhibin will suppress FSH both in vitro and in vivo and that inhibin can be used as an immunogen to raise neutralizing antibodies against inhibin. The immunization of mammals, e.g. cattle and sheep, with the purified preparation of inhibin and a suitable adjuvant leads to the development of antibodies in immunized animals. These antibodies neutralize the animal's own inhibin production, thereby removing the suppressive effect on FSH secretion. The resultant elevation in FSH leads to increased stimulation of follicular development in the ovary with an increase in ovulation rate.

Collection of serum from animals immunized against inhibin also provides an antiserum which can be used for, passive immunization of other animals. By this method, the injection of the inhibin antiserum neutralizes the animal's own inhibin and hence leads to an elevation of FSH and the subsequent events in stimulating ovulation. Both the passive and the active methods of immunization may be used to increase ovulation rate.

The potential to use inhibin for active immunization to achieve gonadal growth is illustrated by the increase in testicular size of the rabbit tested during immunization against inhibin (Example 5).

(ii) Inhibition of ovarian and testicular function: The recognized importance of FSH in the stimulation of follicular development in the ovary and sperm production in the testis (Ross et. al., (1981), in Testbook of Endocrinology, ed. Williams, p. 355; Bardin and Paulsen, (1981), The Testes, in Textbook of Endocrinology ed. Williams, p. 293) supports a potential role for inhibin in the suppression of gonadal function. It is expected that the administration of inhibin will lead to a suppression of ovarian and testicular function and a disruption of fertility. This action of inhibin can be used in males and females of the human, ovine and bovine species and is likely to be applicable to other species.

(iii) Advancement of the onset of fertility: It is recognized that one of the earliest events in the onset of puberty is the rise in FSH levels which leads to ovarian and testicular stimulation (Ross et. al. (1981) in Textbook of Endocrinology, ed. Williams, p. 355; Bardin and Paulsen, (1981), The Testes, in Textbook of Endocrinology, ed. Williams, p. 293). The potential exists that immunization of sexually immature mammals against inhibin, by active or passive techniques, will lead to a premature onset of puberty with attendant stimulation of ovarian and testicular function.

The lifetime reproductive performance of domestic animals such as cows, sheep and pigs depends upon the age of onset of puberty, the intervals between each conception, and the potential for subsequent ovarian failure with advancing age. Immunization of young animals before puberty with inhibin, either by active or passive immunization, neutralises the animal's own inhibin production and leads to an elevation of FSH. This elevation in FSH levels induces pubertal development at an earlier age than normal by stimulation of the gonad. This method can be used to induce precocious puberty in male or female mammals.

(iv) Suppression of puberty: Since FSH is recognized as a crucial factor in the onset of puberty, administration of inhibin may be used as a means of suppressing puberty in unwanted situations, e.g. precocious pubertal development in humans, or in delaying the onset of puberty.

(v) Inhibin can be used as an immunogen to raise antisera or monoclonal antibodies which can be used to develop radioimmunoassays or enzyme-linked immunoassays to measure inhibin, and to develop immunoadsorbent columns to aid in the purification of inhibin.

(vi) Using the above-described antisera a radioimmunoassay system to measure inhibin has been devised which enables the measurement of inhibin in biological samples (e.g. plasma, serum or urine), which is not possible using the previously known in vitro bioassay system of Scott et al (1980). Inhibin levels in plasma or serum will provide an index of Sertoli cell and granulosa cell function for use in the diagnosis of fertile status.

(vii) It is possible that administration of high doses of inhibin may inhibit the secretion of LH. This would further support the ability of inhibin to suppress ovulation.

It will be clearly understood that the invention in its general aspects is not limited to the specific details referred to hereinabove.

We claim:

1. A composition of matter comprising purified inhibin of a purity sufficient to yield a single major band on non-reducing SDS-PAGE, wherein said purified inhibin suppresses production of follicle stimulating hormone without suppressing production of luteinizing hormone.

2. A composition of matter comprising purified proteinaceous material comprising at least one subunit, said subunit having an apparent molecular weight of $14,000 \pm 2,000$, wherein said purified proteinaceous material is of a purity sufficient to yield a single major band on non-reducing SDS-PAGE, and wherein said purified proteinaceous material suppresses production of follicle stimulating hormone without suppressing production of luteinizing hormone.

3. A composition of matter comprising purified proteinaceous material of a purity sufficient to yield a single major band on non-reducing SDS-PAGE, wherein said purified proteinaceous material suppresses cellular content of follicle stimulating hormone without suppressing cellular content of luteinizing hormone.

4. A composition of matter comprising purified proteinaceous material of a purity sufficient to yield a single major band on non-reducing SDS-PAGE, wherein said purified proteinaceous material suppresses cellular content of follicle stimulating hormone in rate anterior pituitary cells in culture without suppressing cellular content of luteinizing hormone.

5. A composition of matter comprising purified proteinaceous material of at least 75% purity, wherein said purified proteinaceous material suppresses production of follicle stimulating hormone without suppressing production of luteinizing hormone.

6. The composition of matter as defined by claim 5, wherein said purified proteinaceous material yields a single major band on non-reducing SDS-PAGE.

7. The composition of matter as defined by any one of claims 1-4, wherein said band is visualized with silver staining.

8. The composition of matter as defined by any one of claims 1-4, wherein said band is visualized with Coomassie blue staining.

9. The composition of matter as defined by any one of claims 1-5, wherein said composition of matter comprises at least a first subunit and a second subunit, and further wherein said first subunit and said second subunit are joined by at least one disulfide bridge.

10. The composition of matter as defined by any one of claims 1–5, wherein said composition of matter has an apparent molecular weight of 56,000±3,000.

11. The composition of matter as defined by claim 10, wherein said composition of matter has an apparent molecular weight of 56,000±1,000.

12. The composition of matter as defined by claim 11, wherein said composition of matter has an apparent molecular weight of about 56,000.

13. The composition of matter as defined by any one of claims 1–3 or 5, wherein said suppression of follicle stimulating hormone occurs in rat anterior pituitary cells in culture.

14. The composition of matter as defined by any one of claims 1–5, wherein said suppression of follicle stimulating hormone is dose-dependent.

15. The composition of matter as defined by any one of claims 1–5, wherein said composition of matter does not suppress thyroid stimulating hormone.

16. The composition of matter as defined by any one of claims 1–5, wherein said composition of matter does not suppress prolactin.

17. The composition of matter as defined by claim 16, wherein said composition of matter does not suppress thyroid stimulating hormone.

18. The composition of matter as defined by claim 17, further wherein said composition of matter does not produce a non-specific, toxic suppression of hormone production.

19. The composition of matter as defined by any one of claims 1–5 wherein said composition of matter is a glycoprotein.

20. The composition of matter as defined by any one of claims 1–5, wherein said composition of matter comprises at least two non-identical subunits.

21. The composition of matter as defined by any one of claims 1–5, wherein said composition of matter is obtained from follicular fluid.

22. The composition of matter as defined by claim 21, wherein said composition of matter is obtained from mammalian follicular fluid.

23. The composition of matter as defined by claim 22, wherein said composition of matter is obtained from ovarian follicular fluid.

24. The composition of matter as defined by claim 22, wherein said composition of matter is obtained from a bovine.

25. The composition of matter as defined by claim 22, wherein said composition of matter is obtained from an ovine.

26. The composition of matter as defined by claim 22, wherein said composition of matter is obtained from a human.

27. The composition of matter as defined by any one of claims 1–5, wherein said composition of matter has a pI of between about 6.9 and 7.3.

28. The composition of matter as defined by any one of claims 1–5, wherein said composition of matter can bind specifically to a gel permeation matrix comprising a bead formed gel prepared from agarose.

29. The composition of matter as defined by any one of claims 1–5, wherein said composition of matter can bind with horseradish peroxidase-labelled wheat germ lectin following fractionation of said composition of matter into fractions on SDS-PAGE and electrotransfer of said fractions to nitrocellulose.

30. A method for producing monoclonal antibodies specific to inhibin, comprising producing said monoclonal antibodies using the composition of matter as defined by any one of claims 1–5 as an immunogen.

31. A composition of matter comprising monoclonal antibodies obtained according to the method as defined in claim 30.

32. A method for assaying for inhibin in a sample, comprising: providing the purified inhibin as defined by claim 1 in radiolabelled form; adding the radiolabelled purified inhibin and antibodies specific to inhibin to the sample; allowing the antibodies to bind to inhibin present in the sample; and separating the antibody-bound from the unbound radiolabelled inhibin.

33. A method for detecting and diagnosing infertility in a mammal, comprising assaying a sample from said mammal by the radioimmunoassay procedure as defined by claim 32.

34. A purified proteinaceous material having a purity sufficient to yield a single major band on non-reducing SDS-PAGE, wherein said purified proteinaceous material suppresses production of follicle stimulating hormone without suppressing production of luteinizing hormone, and which, when administered as an antigen in mammals, raises antibodies that neutralize the follicle stimulating hormone suppressing activity of said purified proteinaceous material.

35. A composition of matter comprising a purified inhibin of a purity sufficient to yield a single major band on non-reducing SDS-PAGE having an apparent molecular weight of between about 54,000 and 57,000, said purified inhibin being capable of suppressing production of follicle stimulating hormone by rat anterior pituitary cells in culture without inhibiting the production of luteinizing hormone by said cells.

36. The composition of matter as defined by claim 35, wherein said apparent molecular weight is between about 55,000 and 57,000.

37. The composition of matter as defined by claim 36, wherein said apparent molecular weight is about 56,000.

38. The composition of matter as defined by claim 35, wherein said purified inhibin comprises at least a first subunit and a second subunit.

39. A composition of matter comprising a first subunit of the composition of matter as defined by claim 38.

40. A composition of matter comprising a second subunit of the composition of matter as defined by claim 38.

41. The composition of matter as defined by claim 38, wherein said second subunit is a glycoprotein.

42. The composition of matter as defined by claim 38, wherein said first subunit has an apparent molecular weight of between about 12,000 and 16,000.

43. The composition of matter as defined by claim 42, wherein said first subunit has an apparent molecular weight of between about 13,000 and 15,000.

44. The composition of matter as defined by claim 43, wherein said first subunit has an apparent molecular weight of about 14,000.

45. The composition of matter as defined by claim 38, wherein said second subunit has an apparent molecular weight of between about 41,000 and 47,000.

46. The composition of matter as defined by claim 45, wherein said second subunit has an apparent molecular weight of between about 43,000 and 46,000.

47. The composition of matter as defined by claim 46, wherein said second subunit has an apparent molecular weight of about 44,000.

48. The composition of matter as defined by claim 38, wherein said purified inhibin comprises a first subunit having an apparent molecular weight of about 14,000 and a second subunit having an apparent molecular weight of about 44,000.

49. A method for purifying inhibin from a starting material containing inhibin comprising:
   a) subjecting said starting material to a first gel permeation chromatography to yield a first eluent;
   b) subjecting said first eluent to a second gel permeation chromatography to yield a second eluent;
   c) subjecting said second eluent to reverse phase high performance liquid chromatography to yield a third eluent; and
   d) subjecting said third eluent to preparative polyacrylamide gel electrophoresis.

50. A composition of matter comprising purified inhibin obtained according to the method as defined by claim 49.

51. The composition of matter as defined by claim 50, wherein said purified inhibin has a specific activity of at least about 3 times greater than the specific activity of said starting material.

52. The composition of matter as defined by claim 51, wherein said purified inhibin has a specific activity of at least about 10 times greater than the specific activity of said starting material.

53. The composition of matter as defined by claim 52, wherein said purified inhibin has a specific activity of at least about 20 times greater than the specific activity of said starting material.

54. The composition of matter as defined by claim 53, wherein said purified inhibin has a specific activity of at least about 50 times greater than the specific activity of said starting material.

55. The composition of matter as defined by claim 54, wherein said purified inhibin has a specific activity of at least about 160 times greater than the specific activity of said starting material.

56. The method as defined in claim 49, wherein said starting material is follicular fluid.

57. The method as defined in claim 56, wherein said starting material is mammalian follicular fluid.

58. The method as defined in claim 57, wherein said starting material is bovine follicular fluid.

59. The method as defined in claim 57, wherein said starting material is ovine follicular fluid.

60. The method as defined in claim 57, wherein said starting material is human follicular fluid.

61. The method as defined in claim 49, further comprising diluting said starting material with ammonium acetate prior to said first gel permeation chromatography.

62. The method as defined in claim 61, wherein said ammonium acetate is used at a concentration of about 0.05M.

63. The method as defined in claim 61, wherein said ammonium acetate has a pH of about 7.0.

64. The method as defined in claim 61, further comprising centrifuging said starting material after said ammonium acetate is added thereto.

65. The method as defined in claim 64, further comprising centrifuging said starting material at about 12,000 g.

66. The method as defined in claim 49, wherein a gel permeation matrix comprising covalently cross-linked allyl dextran and N, N$^1$-methylene bisacrylamide is used to perform said first gel permeation chromatography.

67. The method as defined in claim 49, wherein said first eluent comprises a void volume fraction from said gel permeation chromatography.

68. The method as defined by claim 49, further comprising acidifying said first eluent with acid prior to subjecting said first eluent to said second gel permeation chromatography.

69. The method as defined in claim 68, wherein said acid is acetic acid.

70. The method as defined in claim 69, wherein said first eluent is acidified with acetic acid to a final concentration of about 4.0M.

71. The method as defined in claim 49, wherein a gel permeation matrix comprising a bead formed gel of cross-linked dextran and epichlorohydrin is used to perform said second gel permeation chromatography.

72. The method as defined in claim 49, wherein said second gel permeation chromatography is performed on an analytical column.

73. The method as defined in claim 72, further comprising eluting said second eluent with acetic acid.

74. The method as defined in claim 73, wherein said acetic acid is used at a concentration of about 4.0M.

75. The method as defined in claim 49, further comprising performing said reverse phase high performance liquid chromatography using a chemically-bonded N-alkylsilica column material.

76. The method as defined in claim 75, wherein an Ultrapore RPSC is used for said column.

77. The method as defined in claim 76, wherein said N-alkylsilica column material has a particle size distribution of between about 5 and 10 microns.

78. The method as defined by claim 75, further comprising using a water-miscible organic solvent to produce said third eluent.

79. The method as defined in claim 78, wherein said water-miscible organic solvent is selected from the group consisting of methanol, acetonitrile, and isopropanol.

80. The method as defined in claim 79, further comprising using a gradient of about 0-50% acetonitrile to produce said third eluent.

81. The method as defined in claim 80, wherein said acetonitrile is present in a solution of about 0.1% trifluoroacetic acid.

82. The method as defined in claim 80, wherein said third eluent comprises a portion of said gradient elution corresponding to about 30.0% acetonitrile.

83. The method as defined in claim 78, further comprising modifying said water-miscible organic solvent with an ionic modifier.

84. The method as defined in claim 83, wherein said ionic modifier is selected from the group consisting of trifluoroacetic acid, ammonium bicarbonate, ammonium acetate, and sodium phosphate.

85. The method as defined in claim 49, further comprising dissolving said third eluent in non-reducing sample buffer prior to fractionating said third eluent on a polyacrylamide gel electrophoresis apparatus.

86. The method as defined in claim 85, further comprising incubating said third eluent at about room temperature prior to fractionating.

87. The method as defined in claim 86, wherein said third eluent is incubated at about room temperature overnight prior to fractionating.

88. The method as defined in claim 86, wherein said third eluent is incubated at about room temperature for about one hour prior to fractionating.

89. The method as defined in claim 49, further comprising using, for said preparative polyacrylamide gel electrophoresis, a separation gel; a stacking gel; a non-reducing sample buffer; and an electrophoretic buffer.

90. The method as defined in claim 89, wherein said separating gel comprises Tris-HCl, SDS acrylamide, bis acrylamide, and ammonium persulphate.

91. The method as defined in claim 90, wherein said separating gel comprises about 0.38M Tris-HCl at a pH of about 8.8, 0.1% w/v SDS, 7.5% acrylamide, 0.2% bis acrylamide, and 0.03% ammonium persulphate.

92. The method as defined in claim 89, wherein said stacking gel comprises Tris-HCl, SDS acrylamide, bis acrylamide, ammonium persulphate, and TEMED.

93. The method as defined in claim 92, wherein said stacking gel comprises about 0.125M Tris-HCl at a pH of about 6.8, about 0.1% w/v SDS, about 5% acrylamide, about 0.13% Bis acrylamide, and about 0.1% ammonium persulphate.

94. The method as defined in claim 89, wherein said non-reducing sample buffer comprises Tris-HCl, glycerol, SDS, and bromophenol blue.

95. The method as defined in claim 94, wherein said non-reducing sample buffer comprises about 0.06M Tris-HCl at a pH of about 6.8, about 12.5% glycerol, about 1.25% w/v SDS, and about 0.006% bromophenol blue.

96. The method as defined in claim 89, wherein said electrophoresis buffer comprises tris-glycine buffer containing SDS.

97. The method as defined in claim 96, wherein said electrophoresis buffer comprises about 2.5 mM Tris-glycine buffer containing about 0.05% (w/v) SDS.

98. The method as defined in claim 49, further comprising electrophoresing said third eluent at a current of about 20 mA until said third eluent migrates into said separating gel, and then increasing said current to about 30 mA until said electrophoresis is complete.

99. The method as defined in claim 49, further comprising isolating a gel portion from said preparative polyacrylamide gel electrophoresis containing inhibin and subjecting the inhibin contained in said gel portion to electrophoretic elution.

100. The method as defined in claim 99, wherein said electrophoretic elution comprises:
a) washing said gel portion in an elution buffer;
b) soaking said gel portion in a soaking buffer overlaid with an elution buffer;
c) initiating electrophoretic elution of said gel portion;
d) replacing said elution buffer with a dialysis buffer;
e) continuing electrophoretic elution of said gel portion until said inhibin has migrated out of said gel portion; and
f) collecting said inhibin.

101. The method as defined in claim 100, wherein said elution buffer comprises SDS and $NH_4HCO_3$.

102. The method as defined in claim 101, further wherein said elution buffer comprises about 0.1% SDS in about 0.05M $NH_4HCO_3$.

103. The method as defined in claim 100, wherein said soaking buffer comprises SDS and $NH_4HCO_3$.

104. The method as defined in claim 103, further wherein said soaking buffer comprises about 2% SDS in about 0.4M $NH_4HCO_3$.

105. The method as defined in claim 100, wherein said dialysis buffer comprises SDS and $NH_4HCO_3$.

106. The method as defined in claim 105, further wherein said dialysis buffer comprises about 0.02% SDS in about 0.01M $NH_4HCO_3$.

107. The method as defined in claim 49, wherein purified inhibin of a purity sufficient to yield a single major band on non-reducing SDS-PAGE is obtained.

108. The method as defined in claim 107, wherein said band is visualized with silver staining.

109. The method as defined in claim 107, wherein said band is visualized with Coosmassie blue staining.

110. The method as defined in claim 49, further comprising using, for said preparative polyacrylamide gel electrophoresis, a separation gel; a stacking gel; a reducing sample buffer; and an electrophoretic buffer.

111. The method as defined in claim 110, further comprising preparing said reducing sample buffer by adding about 0.1% 2-mercaptoethanol to a non-reducing sample buffer.

112. A method for producing antibodies specific to inhibin, comprising immunizing a mammal with the preparation of purified inhibin as defined by claim 1 in combination with an adjuvant.

113. A composition of matter, comprising antibodies specific to inhibin produced according to the method as defined by claim 112.

114. The method as defined in claim 112, further comprising the steps of:
a) dissolving said purified inhibin in buffer;
b) emulsifying said purified inhibin dissolved in said buffer to yield an emulsion;
c) injecting said emulsion into said mammal.

115. The method as defined in claim 112, wherein said buffer is a phosphate buffer.

116. The method as defined in claim 115, wherein said phosphate buffer has a pH of about 7.4.

117. The method as defined in claim 115, further comprising emulsifying said purified inhibin dissolved in said phosphate buffer with an approximately equal volume of oil-based adjuvant.

118. The method as defined in claim 114, further comprising injecting said mammal at least a first time and a second time.

119. The method as defined in claim 114, further comprising injecting said mammal at at least one intramuscular site.

120. The method as defined in claim 119, further comprising also injecting said mammal subcutaneously.

121. The method as defined in claim 112, further comprising isolating antisera containing said antibodies from said mammal.

122. A composition of matter comprising antisera containing antibodies specific to inhibin, said antisera being produced according to the method as defined by claim 121.

123. The composition of matter as defined by claim 122, wherein said antisera neutralizes inhibin activity in vitro.

124. The method as defined in claim 121, further comprising isolating said antibodies from said antisera.

125. A composition of matter comprising monoclonal antibodies that preferentially bind to an immunological determinant of the composition of matter as defined by anyone of claims 61–65.

126. The composition of matter as defined by claim 125, wherein said monoclonal antibodies are specific to inhibin.

127. The composition of matter as defined by claim 126, wherein said composition of matter is found in follicular fluid.

128. The composition of matter as defined by claim 127, wherein said follicular fluid is mammalian follicular fluid.

129. The composition of matter as defined by claim 128, wherein said follicular fluid is bovine follicular fluid.

130. The composition of matter as defined by claim 128, wherein said follicular fluid is ovine follicular fluid.

131. The composition of matter as defined by claim 128, wherein said follicular fluid is human follicular fluid.

132. The composition of matter as defined by any one of claims 1-5, wherein said composition of matter is labelled.

* * * * *

UNITED STATES PATENT AND TRADEMARK OFFICE
CERTIFICATE OF CORRECTION

PATENT NO. : 5,102,807

DATED : April 7, 1992

INVENTOR(S) : H. BURGER et al.

It is certified that error appears in the above-identified patent and that said Letters Patent is hereby corrected as shown below:

On the title page, item [75] insert --, Camberwell,-- after "Wettenhall".

On the cover, page 2, column 1, line 33, change "de Kreiser" to ---de Kretser---.

On the cover, page 2, column 2, line 1, change "de Kreiser" to ---de Kretser---.

On the cover, page 2, column 2, line 4, change "de Kreiser" to ---de Kretser---.

On the cover, page 2, column 2, line 21, change "de Kreiser" to ---de Kretser---.

On the cover, page 2, column 2, line 23, change "de Kreiser" to ---de Kretser---.

At column 13, line 59 insert ---concanavalin A bound to--- before "a gel permeation matrix".

At column 16, line 23 change "72" to ---71---.

At column 16, line 30 change "76" to ---75---.

At column 18, line 33 change "112" to ---114---.

UNITED STATES PATENT AND TRADEMARK OFFICE
CERTIFICATE OF CORRECTION

PATENT NO. : 5,102,807
DATED : April 7, 1992
INVENTOR(S) : H. Burger et al.

It is certified that error appears in the above-indentified patent and that said Letters Patent is hereby corrected as shown below:

Column 18, line 65, change "61-65" to read --1-5--.

Signed and Sealed this

Eighth Day of November, 1994

Attest:

BRUCE LEHMAN

Attesting Officer

Commissioner of Patents and Trademarks